United States Patent
Strodtholz et al.

(10) Patent No.: US 10,364,407 B2
(45) Date of Patent: Jul. 30, 2019

(54) KIT AND METHOD FOR CLEANING AND DISINFECTING MEDICAL INSTRUMENTS AND APPLIANCES

(71) Applicant: Chemische Fabrik Dr. Weigert GmbH & Co. KG, Hamburg (DE)

(72) Inventors: Iris Strodtholz, Hamburg (DE); Petra Reessing, Hamburg (DE); Jurgen Staffeldt, Hamburg (DE)

(73) Assignee: CHEMISCHE FABRICK DR. WEIGERT GMBH & CO. KG, Hamburg (DE)

( * ) Notice: Subject to any disclaimer, the term of this patent is extended or adjusted under 35 U.S.C. 154(b) by 0 days.

(21) Appl. No.: 15/023,815

(22) PCT Filed: Jun. 2, 2014

(86) PCT No.: PCT/EP2014/061352
§ 371 (c)(1),
(2) Date: Mar. 22, 2016

(87) PCT Pub. No.: WO2015/043777
PCT Pub. Date: Apr. 2, 2015

(65) Prior Publication Data
US 2016/0230126 A1    Aug. 11, 2016

(30) Foreign Application Priority Data
Sep. 26, 2013 (EP) ...................... 13186209

(51) Int. Cl.
| | |
|---|---|
| C11D 3/386 | (2006.01) |
| C11D 7/32 | (2006.01) |
| C11D 3/30 | (2006.01) |
| C11D 3/33 | (2006.01) |
| C11D 11/00 | (2006.01) |
| A61L 2/18 | (2006.01) |
| B08B 3/08 | (2006.01) |
| B08B 3/10 | (2006.01) |

(52) U.S. Cl.
CPC ............ *C11D 3/38618* (2013.01); *A61L 2/18* (2013.01); *B08B 3/08* (2013.01); *B08B 3/10* (2013.01); *C11D 3/30* (2013.01); *C11D 3/33* (2013.01); *C11D 3/386* (2013.01); *C11D 7/3218* (2013.01); *C11D 7/3245* (2013.01); *C11D 11/0041* (2013.01)

(58) Field of Classification Search
None
See application file for complete search history.

(56) References Cited

U.S. PATENT DOCUMENTS

| | | | |
|---|---|---|---|
| 4,243,546 A | 1/1981 | Shaer | |
| 4,835,804 A | 6/1989 | Arunau-Munoz et al. | |
| 5,858,117 A * | 1/1999 | Oakes | C11D 1/008 134/26 |
| 6,197,739 B1 * | 3/2001 | Oakes | C11D 1/008 510/111 |

FOREIGN PATENT DOCUMENTS

| | | | |
|---|---|---|---|
| CN | 1158633 A * | 9/1997 | ............. C11D 1/008 |
| EP | 0481663 | 1/1996 | |
| EP | 1241112 | 9/2002 | |
| EP | 1327674 | 6/2008 | |
| GB | 2339795 | 2/2000 | |
| WO | WO 2013004635 | 1/2013 | |

OTHER PUBLICATIONS

EPO machine translation of CN1158633 retrieved from https://worldwide.espacenet.com/publicationDetails/biblio?CC=CN&NR=1158633A&KC=A&FT=D&ND=3&date=19970903&DB=&locale=en_EP# on Aug. 21, 2017.*
EPO machine translation of EP1327674, retrieved from https://worldwide.espacenet.com/publicationDetails/biblio?CC=EP&NR=1327674A1&KC=A1&FT=D&ND=3&date=20030716&DB=&locale=en_EP (Year: 2018).*
Mifflin, 2X Detergents—Conveniently Concentrated. Why Less is Better for You and the Environment. Retrieved from https://web.archive.org/web/20080407160630/http://housewares.about.com/od/sewinglaundry/qt/2Xdetergents.htm. Apr. 2008. 1 page.
International Search Report and Written Opinion for PCT/EP2014061352, dated Aug. 20, 2014. With English translation. 12 pages.

* cited by examiner

*Primary Examiner* — Eric W Golightly
(74) *Attorney, Agent, or Firm* — Casimir Jones, S.C.; Mary Ann D. Brow

(57) ABSTRACT

A kit for mechanically cleaning and/or disinfecting medical and/or surgical instruments and/or devices, the kit containing a first component containing at least 15 wt. % alkanolamine and at least 10 wt. % complexing agent, and a second component containing at least one enzyme; and a method of cleaning such instruments and devices using the components of the kit.

20 Claims, No Drawings

KIT AND METHOD FOR CLEANING AND DISINFECTING MEDICAL INSTRUMENTS AND APPLIANCES

This application is a § 371 US National Entry of International Application No. PCT/EP2014/061352, filed Jun. 2, 2014, which claims the benefit of European Application No. 13186209.6, filed Sep. 26, 2013.

FIELD OF THE INVENTION

The invention relates to a kit and a method for machine cleaning and/or disinfecting of medical and/or surgical instruments and/or appliances.

BACKGROUND OF THE INVENTION

In the hospital, surgical instruments and also other medical equipment are customarily cleaned by machine by using alkaline cleaning compositions, and then disinfected chemically or thermally. Such strongly alkaline compositions may act aggressively toward sensitive surfaces. Immediately after they have been used, surgical instruments with contamination from blood are frequently placed, for example, into a disinfecting solution, where they initially remain until cleared out into the washing machine for cleaning. The disinfectant causes the blood to coagulate, and the active disinfecting ingredient causes denaturing of the protein constituents present in the blood. Particularly persistent blood residues of this kind are frequently removable only by means of alkaline active chlorine-containing cleaning compositions. The oxidizing active chlorine component brings about the decomposition of the denatured protein constituents. Other constituents of disinfectants as well, such as iodine, for example, may form residues that are difficult to remove.

The alkaline active chlorine-containing cleaners have the disadvantages that they comprise hazardous substances liable to declaration, that their handling necessitates special precautionary measures in order to protect the operating personnel, and that they constitute an unwanted environmental pollution in the wastewater.

U.S. Pat. No. 4,243,546, EP-A-0 481 663, and EP-A-0 730 024 disclose enzyme-containing cleaning compositions which are able to bring about enzymatic degradation of blood proteins in particular.

EP-A-1 021 519 discloses an enzyme-free cleaning composition concentrate for cleaning surgical instruments. A disadvantage stated for the enzymatic cleaners therein is that the enzyme activity may subside in the course of prolonged storage.

EP-A-1 327 674 discloses a cleaning composition concentrate for medical instruments that comprises an alkanolamine, enzymes, and aminopolycarboxylic acids as complexing agents.

SUMMARY OF THE INVENTION

It is an object of the invention to provide a possibility for effective cleaning of medical and surgical instruments and appliances that is easy to operate in practice and requires the holding only of small volumes of cleaning compositions.

The invention achieves this object by means of a kit for the machine cleaning and/or disinfecting of medical and/or surgical instruments and/or appliances, characterized in that it comprises:

a. a first component which comprises at least 15 wt % of alkanolamine and at least 10 wt % of complexing agent;
b. a second component which comprises at least one enzyme.

Definitions

An explanation will first be given of a number of terms used in the context of the invention.

Cleaning and/or disinfecting compositions for medical and/or surgical elements and appliances are compositions which at least reduce the soiling and microbial load involved in the processing of such instruments.

Machine cleaning takes place in a suitable washing machine, preferably in a customary washer-disinfector for medical and/or surgical instruments (WD). This term is defined in ISO 15883-1.

DESCRIPTION OF THE INVENTION

The kit of the invention comprises at least two components. The first component (also called alkali component) contains relatively high concentrations of alkanolamine and complexing agent. The second component (also called enzyme component) comprises at least one enzyme, preferably a proteolytic enzyme. The amount of these proteolytic enzymes is preferably between 0.05 and 1 Anson unit per g of component.

Surprisingly it has emerged that by dividing these fundamentally known constituents of a cleaning composition over two components in the manner claimed it is possible to achieve very effective cleaning and/or disinfecting of medical instruments with very small amounts of active ingredient and also, above all, with very small volumes employed of the two components.

As will be elucidated further below in the examples, a mixture, prepared in a volume ratio of one to one, of two components of the kit according to the invention, for example, can be made up as a 0.2% strength aqueous solution and has effective activity with respect to the customary mixed forms of soiling on surgical instruments.

In accordance with the invention it is therefore possible, in hospital operation, to stock the components of the kit in reservoir vessels having a content of, for example, 5 to 20 l. Vessels or canisters of this kind are easy to transport and in operation can be stored and connected in the immediate vicinity of the washer-disinfector used. In accordance with the invention there is no need to stock large volumes for a sufficient operating period, in the form of drums of 200 l capacity, for example, which generally require a costly and inconvenient system of supply lines, since drums of such capacity can typically not be stored directly adjacent to the cleaning and disinfecting apparatus, but must instead be disposed in a separate storage room and connected accordingly via long lines to the consuming location. Surprisingly it has emerged that the use of an alkanolamine as a constituent of the alkaline component in the minimum concentration claimed leads to particularly high activity in conjunction with very low dosing amounts or concentrations of the components of the kit into the aqueous cleaning solution. The separation of the constituents of the cleaning and/or disinfecting composition, provided for in accordance with the invention, over two components permits the provision of what are called high concentrates, in which ingredients that are incompatible or poorly compatible with one another (for example, alkaline alkanolamines on the one hand and enzyme on the other hand) can be stably stored and stocked in higher concentrations than in the case of a cleaning composition having only one component.

The alkanolamine content of the first component in one preferred embodiment of the invention is 15-30 wt %, more preferably 15-25 wt %. The alkanolamine may preferably have the following structure:

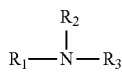

where $R_1$ is a hydroxyalkyl group having 1 to 6 C atoms and where $R_2$ and $R_3$ independently of one another are the stated hydroxyalkyl group or hydrogen.

More preferably the alkanolamine is selected from the group consisting of mono-, di- and/or triethanolamine. The first component may comprise preferably 10-30 wt %, more preferably 15-25 wt %, of complexing agent. The complexing agents serve for water softening and, by complexing alkaline earth metal ions are able to improve the cleaning activity relative to typical theater contaminants. The complexing agents may comprise homo-, co- or terpolymers based on acrylic acid or alkali metal salts thereof, or else phosphonic acids and/or alkali metal salts thereof, such as 1-hydroxyethane-1,1-diphosphonic acid, aminotris-methylenephosphonic acid, ethylenediaminotetrakis-methylenephosphonic acid, phosphonobutanetricarboxylic acid, for example; tartaric acid, citric acid, and gluconic acid; and also nitrilotriacetic acid or ethylenediaminetetraacetic acid and/or salts thereof.

Preference is given to the use of chelating agents, especially amino(poly)carboxylic acids and also salts thereof, an example being the trisodium salt of methylglycinediacetic acid (MGDA).

The corrosive effect of complexing agents on anodized aluminum surfaces and the like may be alleviated or avoided completely through the addition of at least one monoester and/or diester of phosphoric acid with aliphatic alcohols of chain length $C_1$ to $C_{22}$ and/or aliphatic diols and/or aliphatic polyols of chain length $C_2$ to $C_{22}$. Particularly preferred is a diester of phosphoric acid with butanol on the one hand and ethylene glycol on the other. This ester is available commercially under the designation Hordaphos® MDGB. In accordance with the invention a good cleaning effect is obtained in this way even when using hard water, with a gentle action nevertheless on anodized aluminum areas. The second component may comprise at least one proteolytic enzyme. Suitable proteolytic enzymes are available for example from Novozymes under the designation Esperase® 8.0 L, Subtilisin®, or Liquanase® Ultra 2.0 L.

The second component may in accordance with the invention comprise surfactants, preferably nonionic surfactants. The addition of anionic and cationic surfactants is likewise possible.

The nonionic surfactants may be selected in accordance with the invention from the group consisting of fatty alcohol ethoxylates, fatty alcohol propoxylates, EO-PO block copolymers, alkylglucosides, alkylpolyglucosides, octylphenol ethoxylates, and nonylphenol ethoxylates. Ethoxylated and/or propoxylated fatty alcohols that are familiar to the skilled person are particularly preferred. Nonionic surfactants of this kind are available, for example, from the companies Cognis or Julius Hoesch.

Customary preservatives can be added to the second component, in particular, examples being p-hydroxybenzoic acid or its methyl ester, 5-bromo-5-nitro-1,3-dioxane, salicylic acid, 2-naphthyl m-N-dimethylthio-carbanilate, 5-chloro-5-methyl-4-isothiazolin-3-one, 2-methyl-4-isothiazolin-3-one, cetyltrimethylammonium chloride (CTAC), and mixtures of these compounds. A further preservative is p-hydroxybenzoic acid or its methyl ester. By means of these preservatives it is possible to avoid microbial and fungal infestation of the components.

As and when required, formulating assistants (solubilizers) may be added, such as sodium cumenesulfonate, sodium toluenesulfonate, sodium xylenesulfonate, urea, glycols, more particularly polypropylene glycols and polyethylene glycols, methylacetamide, and fatty alcohols, such as cetyl alcohol, for example.

The listing of possible ingredients is not final. It is possible additionally, for example, to add wetting agents, emulsifiers, foam inhibitors, or the like. Advantageous, for example, is the addition of N-acyl-glutamate as wetting agent.

A further subject of the invention is the use of a kit of the invention for the machine cleaning and/or disinfecting of medical and/or surgical instruments and/or appliances.

Such machine cleaning takes place without human input during an automatic program sequence, particularly in a customary instrument cleaner (WD). The "cleaning and/or disinfecting" feature is intended to express the fact that the kit of the invention can be used both in combined cleaning and disinfecting in a single process step and also in program sequences where a cleaning step is followed by a separate disinfecting step. In this case the kit of the invention can be used in both these steps.

Likewise a subject of the invention is a method for cleaning medical and/or surgical instruments and/or appliances, characterized by the following steps:
 a) applying a 0.05% to 0.5% strength aqueous solution of the components of a kit of the invention,
 b) leaving the solution to act at a temperature from room temperature up to the boiling temperature of the solution,
 c) rinsing.

With the method of the invention, the applying of the aqueous solution of the cleaning composition concentrate occurs preferably by spraying, but may alternatively take place, for example, by immersion or watering. The percentages are weight percentages, unless indicated otherwise in the specific instance.

The leaving of the cleaning solution to act following its application may comprise action at rest, i.e., without ongoing application or spray application or mechanical circulation or moving of the cleaning solution. Preference is given in the course of the machine cleaning and/or disinfecting to continuous or interrupted circulation of the cleaning solution in the WD used, where the solution is preferably rinsed or sprayed continuously onto the appliances and/or instruments.

The components of the kit may be metered directly into the aqueous solution used as cleaning liquor.

The leaving to act in step b) takes place preferably at room temperature to 55° C., preferably at 35 to 50° C., more preferably at 40 to 50° C.

The aqueous solution of the components of the kit preferably has a pH of 9 to 11, more preferably 10 to 11. Where pH values of a diluted solution of the cleaning composition concentrate are measured for the purposes of the present specification, the solvent used is fully deionized water (DI) water. If the concentrate is made up with customary mains water into a ready-to-use solution, there may be slight deviations in pH values depending on the nature of that water.

Adjusting the pH of the concentrates/components to the desired range is accomplished, where appropriate, preferably by addition of acids and/or suitable buffer systems. Preferred is the addition of at least one organic acid selected from the group consisting of mono-, di- or tricarboxylic acids having 2 to 6 C atoms. Preferred among these acids are citric acid, tartaric acid, malic acid, lactic acid, glycolic acid, glyoxylic acid, succinic acid, adipic acid, and glutaric acid. Citric acid is particularly preferred. The acids are added preferably in small amounts to the concentrate. Some of these stated organic acids, such as citric acid, for example, are at the same time complexing agents in the sense of the invention.

The activity time in step b) is preferably 1 min to 30 min, more preferably 3 to 20 min, more preferably 5 to 15 min.

In the context of the method of the invention it is possible, before the beginning of the cleaning operation, for the type of the medical instruments and appliances to be recognized by suitable technical measures and for a suitable cleaning and disinfecting method to be selected depending on this type. The cleaning and disinfecting equipment for the method of the invention may in accordance with the invention have a program control for implementing a plurality of different cleaning and disinfecting methods. This program control is designed for the appropriate metering of the two components depending on the cleaning and disinfecting method being conducted. The programs may preferably feature different concentrations of the two components, and the ratio of the components used to one another may also be set differently. For example, when processing conventional surgical instruments, a higher concentration of the alkali component may be selected than when processing sensitive instruments for minimally invasive surgery (MIS instruments), or endoscopes. The volume ratio of the two components to one another may in accordance with the invention be preferably between 1:10 and 10:1, more preferably 1:5 and 5:1, more preferably 1:2 and 2:1. In the case of standard cleaning and/or disinfecting, the ratio may for example be 1:1. The concentration of both components together in the cleaning solution for the method of the invention is between 0.05 and 0.5 wt %, preferably 0.08 and 0.3 wt %. Preferred ranges for each individual one of the two components are 0.02 to 0.3 wt %, more preferably 0.04 and 0.15 wt %.

The various programs and the components used in each of them, and also the concentrations and concentration ratios of these components, may be validated as approved operations for the processing of medical products. Possible in that case is the simple and complete documentation of all the processing operations, including the nature, amount and also, where appropriate, batch numbers of the components used.

In accordance with the invention, provision may be made for a means to be provided for recognizing the type of the medical instruments and apparatus to be cleaned and disinfected, and for selecting a suitable cleaning and disinfecting method and/or program depending on this type. This procedure may make sense especially when batches of identical or similar instruments are being cleaned in each case, as for example customary surgical instruments, MIS instruments, or the like. The type of the instruments may be recognized mechanically or optically, as for example by scanning the height in the instrument basket, optically recognizing the instruments, or the like. It is preferred if there are coding devices present either on the instruments themselves or on the baskets with which they are conveyed into the washer-disinfector, these coding devices interacting with corresponding reading devices in the washer-disinfector. Such devices may for example be RFID tags and RFID readers.

With the method of the invention, the type of the instruments and appliances may be selected from the group consisting of conventional surgical instruments, instruments for minimally invasive surgery, endoscopes and parts thereof, instruments for neurosurgery, instruments for ophthalmic surgery, anesthesia utensils, containers for medical instruments and appliances, and theater shoes.

EXPERIMENTAL EXAMPLES

The invention is elucidated below with working examples.

Example 1

An alkali component in accordance with the invention is prepared on the basis of the information in the table below. The amounts of the starting materials to be used are given in parts by weight.

| | |
|---|---|
| Triethanolamine 99% | 20.0 |
| MDGB[1] | 2.0 |
| KOH, 45% | 3.0 |
| MGDA 3 Na, 40% | 40.0 |
| Acumer ® 2000[2] | 3.5 |
| Water (fully deionized) | 31.5 |
| pH of the concentrate | 11.8 |
| pH of a 0.1% strength aqueous solution (in DI water) | 10.8 |

[1]Diester of phosphoric acid with butanol and ethylene glycol
[2]Complexing agent based on carboxylate/sulfonate acrylic copolymers, from Rohm and Haas pH of a 0.1% strength aqueous solution 10.8 (in DI water)

An enzyme component in accordance with the invention is prepared as follows:

| | |
|---|---|
| Na cumenesulfonate 40% | 5.0 |
| Subtilisin | 10.0 |
| FA C12/C14; 2EO/4PO[3] | 0.8 |
| FA C12/C14; 5EO/4PO | 3.0 |
| FA C12/C15; 2EO/6PO | 0.1 |
| CTAC | 0.2 |
| Mixture citric/malic acid 40% | 0.28 |
| KOH, 45% | 0.02 |
| Water (fully deionized) | 80.6 |
| pH of the concentrate | 11.8 |
| pH of a 0.1% strength aqueous solution (in DI water) | 10.8 |

[3]Ethoxylated/propoxylated fatty alcohols

Example 2

This example tests the cleaning performance of the invention.

Rough DIN metal plaques measuring 1×9 cm were used as substrate for test soiling.

10 ml of heparinized ram's blood (from Acila) are mixed with 1 ml of DI water and rendered coagulable again with 150 µl of protamine sulfate (1000 I.U./ml to inactivate 1000 I.U. of heparin in each case). The blood prepared accordingly was applied to the metal plaques and dried at room temperature overnight.

A 1000 ml glass beaker was charged with 900 ml of cleaning solution. This cleaning solution contained in accordance with the invention 0.1 vol % of each of the two components of Example 1. In a second glass beaker, the cleaning solution contained, as a comparative example, 1 vol % of the concentrate of Example 1 from EP 1 327 674 A1 (comparative example).

The cleaning solutions were heated to 55° C. and stirred with a magnetic stirrer on setting 3.5. The metal plaques were immersed into the solutions for 5 minutes and then rinsed off with DI water. Subsequently the metal plaques were dried overnight, inspected, then stained with 0.1% strength amido black solution to test for remaining residues of proteins, and inspected again.

The cleaning performance achieved in accordance with the example of the invention was identical to the cleaning performance of the comparative example. This example therefore demonstrates that with substantially lower concentrations of cleaning compositions than in the prior art employed as comparative example, and hence also with only a fraction of the volumes of cleaning components used, an equally good cleaning performance can be achieved. This is surprising and could not have been inferred from the prior art.

Example 3

In the case of cleaning and/or disinfecting in a WD, the cleaning solution is to be pumped as effectively as possible in circulation. This circulation pumping may be hindered by unwanted foaming of the surfactants used, resulting in a drop in the pump pressure and an adverse effect on circulation.

Because the components of the kit of the invention are used at much lower concentrations than prior-art cleaning compositions, the expectation is that this unwanted foaming will occur to a lesser extent than in the prior art.

In order to verify this, the circulation pumping pressure was measured when pumping the cleaning solution in the low-temperature range at 30° C. in a Miele PG 8536 WD. In this temperature range, which occurs during the heating of the liquor, the solution is particularly sensitive to foaming.

It emerged that a solution containing 0.1 vol % of each of the two components of a kit according to the invention exhibits only a very slight drop in pumping pressure, whereas a solution according to the prior art (1 vol % of Example 1 from EP 1 327 674 A1) exhibited a more significant drop in pumping pressure.

The invention claimed is:

1. A kit for machine cleaning and/or disinfecting of medical and/or surgical instruments and/or appliances, characterized in that it comprises:
   a) a first component which comprises 15 to 30 wt % of alkanolamine, wherein the alkanolamine comprises mono-, di-, and/or triethanolamine, and 10 to 30 wt % of complexing agent; and
   b) a second component which comprises at least one enzyme.

2. The kit as claimed in claim 1, characterized in that the alkanolamine content is 15 to 25 wt %.

3. The kit as claimed in claim 1, characterized in that the alkanolamine has the following structure:

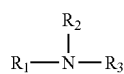

where $R_1$ is a hydroxyalkyl group having 1 to 6 C atoms, and where $R_2$ and $R_3$ independently of one another are the stated hydroxyalkyl group or hydrogen.

4. The kit as claimed in claim 1, characterized in that the first component comprises 15 to 25 wt % of complexing agent.

5. The kit as claimed in claim 1, characterized in that it comprises, as complexing agent, chelating agents.

6. The kit as claimed in claim 1, characterized in that the second component comprises at least one proteolytic enzyme.

7. The kit as claimed in claim 1, characterized in that the second component comprises surfactants.

8. The use of a kit as claimed in claim 1 for machine cleaning and/or disinfecting of medical and/or surgical instruments and/or appliances.

9. A method for cleaning medical and/or surgical instruments and/or appliances, characterized by the following steps:
   a) applying a 0.05% to 0.5% strength aqueous solution of the components of a kit as claimed in claim 1,
   b) leaving the solution to act at a temperature from room temperature up to the boiling temperature of the solution, and
   c) rinsing.

10. The method as claimed in claim 9, characterized in that the leaving to act in step b) occurs at room temperature to 55° C.

11. The method as claimed in claim 9, characterized in that the aqueous solution of the components of the kit has a pH of 9 to 11.

12. The method as claimed in claim 9, characterized in that the time to act in step b) is 1 min to 30 min.

13. The method as claimed in claim 9, characterized in that it further comprises the steps of recognizing the type of the medical instruments and appliances, and of selecting a suitable cleaning and disinfecting method depending on this type.

14. The method as claimed in claim 13, characterized in that the type of the instruments and appliances is selected from the group consisting of conventional surgical instruments, instruments for minimally invasive surgery, endoscopes and parts thereof, instruments for neurosurgery, instruments for ophthalmic surgery, anesthesia utensils, containers for medical instruments and appliances, and theater shoes.

15. The kit as claimed in claim 5, characterized in that the chelating agents are selected from the group consisting of aminopolycarboxylic acids and salts thereof.

16. The kit as claimed in claim 7, characterized in that the surfactants comprise nonionic surfactants.

17. The method as claimed in claim 9, characterized in that the leaving to act in step b) occurs at 35 to 50° C.

18. The kit as claimed in claim 9, characterized in that the aqueous solution of the components of the kit has a pH of 10 to 11.

19. The method as claimed in claim 9, characterized in that the time to act in step b) is 3 to 20 min.

20. The method as claimed in claim 9, characterized in that the time to act in step b) is 5 s to 15 min.

* * * * *